United States Patent
Baig et al.

(10) Patent No.: US 9,161,895 B1
(45) Date of Patent: Oct. 20, 2015

(54) COMPOSITIONS AND METHODS FOR IMPROVING OVERALL TOOTH HEALTH AND APPEARANCE

(71) Applicant: The Procter & Gamble Company, Cincinnati, OH (US)

(72) Inventors: Arif Ali Baig, Mason, OH (US); Robert Vincent Faller, Loveland, OH (US); George Endel Deckner, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 14/806,700

(22) Filed: Jul. 23, 2015

Related U.S. Application Data

(63) Continuation of application No. 12/140,501, filed on Jun. 17, 2008.

(51) Int. Cl.
| | | |
|---|---|---|
| A61K 6/00 | (2006.01) | |
| A61K 8/55 | (2006.01) | |
| A61K 8/49 | (2006.01) | |
| A61K 8/41 | (2006.01) | |
| A61K 8/19 | (2006.01) | |
| A61Q 11/00 | (2006.01) | |

(52) U.S. Cl.
CPC ... A61K 8/55 (2013.01); A61K 8/19 (2013.01); A61K 8/416 (2013.01); A61K 8/4926 (2013.01); A61Q 11/00 (2013.01)

(58) Field of Classification Search
CPC .................................................. A61K 6/0067
See application file for complete search history.

(56) References Cited

U.S. PATENT DOCUMENTS

| | | | |
|---|---|---|---|
| 4,036,950 A | 7/1977 | Baines et al. | |
| 4,152,421 A | 5/1979 | Tsutsumi et al. | |
| 4,243,658 A | 1/1981 | Chang | |
| 4,264,580 A | 4/1981 | Barberio | |
| 4,304,766 A | 12/1981 | Chang | |
| 4,350,680 A | 9/1982 | Harvey et al. | |
| 4,366,146 A | 12/1982 | Chang | |
| 4,428,930 A | 1/1984 | Chang | |
| 4,431,630 A | 2/1984 | Morton | |
| 4,448,766 A | 5/1984 | Morton | |
| 4,470,964 A | 9/1984 | Chang | |
| 4,485,090 A | 11/1984 | Chang | |
| 4,510,127 A | 4/1985 | Chang | |
| 5,019,373 A | 5/1991 | Carter et al. | |
| 5,139,781 A | 8/1992 | Birtwistle et al. | |
| 5,180,579 A | 1/1993 | Birtwistle et al. | |
| 5,244,651 A | 9/1993 | Kayane et al. | |
| 5,370,865 A | 12/1994 | Yamagishi et al. | |
| 5,374,418 A | 12/1994 | Oshino et al. | |
| 5,605,676 A | 2/1997 | Gaffar et al. | |
| 5,624,906 A | 4/1997 | Vermeer | |
| 5,686,403 A | 11/1997 | Matsumoto et al. | |
| 5,824,289 A | 10/1998 | Stoltz | |
| 6,110,445 A | 8/2000 | Gaffar et al. | |
| 6,262,130 B1 | 7/2001 | Derian et al. | |
| 6,566,408 B1 | 5/2003 | Cotrell et al. | |
| 6,685,920 B2 | 2/2004 | Baig et al. | |
| 6,713,049 B1 | 3/2004 | White, Jr. et al. | |
| 6,821,944 B2 | 11/2004 | Reierson et al. | |
| 7,238,652 B2 | 7/2007 | Carnali et al. | |
| 7,241,724 B2 | 7/2007 | Carnali et al. | |
| 7,550,419 B2 | 6/2009 | Futterer et al. | |
| 2002/0041852 A1 | 4/2002 | Napolitano et al. | |
| 2003/0215401 A1 | 11/2003 | Estrada et al. | |
| 2004/0185027 A1 | 9/2004 | Reierson et al. | |
| 2005/0042183 A1 | 2/2005 | Kato et al. | |

FOREIGN PATENT DOCUMENTS

| | | |
|---|---|---|
| GB | 1475251 A | 6/1977 |
| JP | 05-320032 A2 | 12/1993 |
| JP | 10-298044 A2 | 11/1998 |
| WO | WO 2008/049878 A1 | 5/2008 |

OTHER PUBLICATIONS

Olson, J. et al., "Inhibition of *Streptococcus* mutans adherence to hydroxyapatite with combinations of alkyl phosphates and nonionic surfactants," Caries Research 1991:25(1):51-7.

Olson, J. et al., "Surface modification of hydroxyapatite to avoid bacterial adhesion," Colloid & Polymer Science, vol. 269, No. 12, Dec. 1991.

Olson, J. et al., "Inhibition of *Streptococcus* mutans Adherence by Means of Surface Hydrophilization," Journal of Dental Research. vol. 69, No. 9, 1586-1591 (1990).

*Primary Examiner* — Benjamin Packard
(74) *Attorney, Agent, or Firm* — Amanda T. Barry

(57) ABSTRACT

Disclosed are oral care compositions comprising selected surface-active organophosphate compounds and methods of use to provide protection of teeth from erosion caused by the action of chemicals, such as harsh abrasives and acids. The surface-active organophosphate compounds are substantive to teeth, the phosphate groups binding the calcium in teeth and thus preventing loss of calcium from dissolution when contacted with acids. The organophosphate compound may also deposit a protective surface coating that prevents contact of teeth with erosive challenges. Selected organophosphate compounds contain one or more phosphate groups and are combined in the oral care composition with one or more of a fluoride ion agent, an antimicrobial agent preferably selected from quaternary ammonium compounds and polyvalent metal salts, an anticalculus agent and additional surfactant, to provide benefits including superior anti-erosion, anticaries, antiplaque and anti-staining as demonstrated by enhanced fluoride uptake, remineralization, resistance to acid demineralization and antimicrobial activities, resulting in improved overall tooth health, structural integrity and appearance.

18 Claims, No Drawings

COMPOSITIONS AND METHODS FOR IMPROVING OVERALL TOOTH HEALTH AND APPEARANCE

CROSS-REFERENCE TO RELATED APPLICATIONS

This application is a Continuation of U.S. application Ser. No. 12/140,501, filed Jun. 17, 2008; which is a Continuation-in-Part of U.S. application Ser. No. 10/737,425, filed Dec. 16, 2003; which is a Continuation-in-Part of U.S. application Ser. No. 10/319,108, filed Dec. 13, 2002 and issued as U.S. Pat. No. 6,685,920 on Feb. 3, 2004; which is a Continuation-in-Part of U.S. application Ser. No. 09/710,250, filed Nov. 10, 2000 and issued as U.S. Pat. No. 6,713,049 on Mar. 30, 2004; and which claims the benefit of U.S. Provisional Application No. 60/165,351, filed Nov. 12, 1999.

TECHNICAL FIELD

The present invention relates to oral care compositions and methods of use to improve and maintain overall tooth health and appearance. The present compositions comprise combinations of oral care ingredients that act together to provide benefits including antimicrobial, antiplaque, antigingivitis, mineralization and increased fluoride uptake, anticaries, anticalculus, antisensitivity, and antistaining along with improved resistance of teeth to erosive demineralization or dissolution and prevention of tooth damage from subsequent exposure to erosive chemicals such as acidic foods and beverages.

BACKGROUND OF THE INVENTION

Oral care products such as toothpastes and mouthwashes are routinely used by consumers as part of their oral care hygiene regimens. Oral care products are formulated to provide both therapeutic and cosmetic hygiene benefits. Therapeutic benefits include caries prevention which is typically delivered through the use of various fluoride salts; gingivitis prevention by the use of antimicrobial agents such as triclosan, cetylpyridinium chloride, stannous fluoride, zinc citrate or essential oils; and hypersensitivity control through the use of ingredients such as strontium chloride, stannous fluoride or potassium nitrate. Cosmetic benefits include control of plaque and calculus formation, removal and prevention of tooth stain, tooth whitening, breath freshening, and overall improvements in mouth feel impression which can be broadly characterized as mouth feel aesthetics. For example, agents such as pyrophosphate salts have been used as antitartar agents and polymeric agents such as condensed phosphorylated polymers, polyphosphonates, and carboxylated polymers have been used in oral care compositions to provide benefits including tooth surface conditioning and control of tartar, staining and astringency. To illustrate further, commonly assigned U.S. Pat. No. 6,555,094 to Glandorf, et al. discloses oral care compositions comprising a stannous ion source, a fluoride ion source, and a polymeric mineral surface active agent that binds stannous, wherein the compositions provide effective antimicrobial activity for reducing plaque and gingivitis with minimal side effects of tooth staining and astringency. The compositions simultaneously provide reduction and control of supragingival calculus. Additional disclosures related to the use of polyphosphate as mineral surface active agent in oral care compositions include commonly assigned U.S. Pat. No. 5,939,052; U.S. Pat. No. 6,187, 295; U.S. Pat. No. 6,350,436; and U.S. Pat. No. 6,190,644.

Another benefit that is increasingly important for complete oral health is providing protection and resistance of teeth against erosion and wear, which is a permanent loss of tooth substance from the surface due to the action of chemicals, such as harsh abrasives and acids. Dental erosion may be caused by extrinsic or intrinsic factors. Extrinsic erosion is the result of oral consumption of dietary acids such as acidic beverages or fruit juices and environmental factors such as exposure to airborne contamination or acidic water in swimming pools. Intrinsic erosion is caused for example by endogenous acids produced in the stomach and which contact the teeth during the processes of vomiting, regurgitation or reflux. The main cause of regurgitation and induced vomiting are eating disorder conditions such as nervous vomiting, anorexia or bulimia (Moss, 1998, *Int. Den. J.*, 48, 529).

The incidence and severity of dental erosion is on the rise with the increase in the consumption of acidic beverages and juices. The pH and titratable acidity of acidic beverages have been identified as the main causative agents in the initiation and progression of dental erosion (Lussi, 1995, *Caries Res.* 29, 349). Thus methods have been disclosed to modify acidic food and beverage products in order to prevent their erosive effect on teeth. See for example, U.S. Pat. No. 5,108,761 and WO 01/52796 both assigned to The Procter & Gamble Company; U.S. Pat. No. 6,383,473; U.S. Pat. No. 6,319,490; WO 01/72144; and WO 00/13531 all assigned to SmithKline Beecham; CA 1018393 assigned to General Foods Corporation; U.S. Pat. No. 3,471,613 and BE 638645, both assigned to Colonial Sugar Refining Co; and U.S. Pat. No. 4,853,237 assigned to Sinebrychoff Oy. In addition there have been disclosures of oral care compositions comprising agents indicated to provide teeth with antierosion or acid resistance benefits. See for example, JP 2001/158725; U.S. Pat. No. 4,363,794 and U.S. Pat. No. 4,335,102 all assigned to Lion Corporation; U.S. Pat. No. 5,130,123 assigned to The University of Melbourne; WO 99/08550 and WO 97/30601 both assigned to SmithKline Beecham; U.S. Pat. No. 3,914,404, assigned to Dow Chemical Co.; and U.S. Pat. No. 3,105,798, assigned to The Procter & Gamble Co.

One mechanism to provide erosion protection and maintain tooth integrity is described in U.S. Pat. No. 6,685,920 by use of oral compositions comprising certain chemical agents that have affinity for the tooth surface. These agents either bind to the tooth surface or form insoluble compounds or complexes on the tooth surface, thereby forming a protective film or coating. Examples of useful agents are polymeric mineral surface active agents such as phosphorylated polymers, in particular polyphosphates that bind to teeth, or metal ions such as stannous, zinc or copper that form insoluble compounds that deposit onto teeth, and combinations thereof. The polymeric coating or insoluble precipitate deposited onto teeth act as a protective layer that prevents erosive chemicals from contacting the tooth surface and etching away tooth hard tissue.

Caries is another condition that is detrimental to tooth health and structural integrity. The tooth caries process results in calcium phosphate mineral loss from tooth substrate induced by localized plaque microbiological acid production from fermentable dietary substrates. If left uninhibited, the caries process results in sufficient mineral loss from teeth, which manifests as a loss of structural integrity and the formation of a cavity. (G. H. Nancollas, "*Kinetics of de- and remineralization*," pp 113-128; A. Thylstrup, J. D. B. Featherstone and L. Fredebo, "*Surface morphology and dynamics of early enamel caries development*," pp 165-184 in: *Demineralisation and Remineralisation of the Teeth*, IRL Press Ltd., (1983). S. A. Leach and W. M. Edgar, editors). The caries process is not continuous but is described by cyclic periods of mineral loss from teeth, particularly following ingestion of fermentable carbohydrates, followed by periods of no mineral loss or even mineral repair of damaged local regions. Remineralization refers to the process of repair of acid damaged tooth structure—by the recrystallization of mineral salts on the tooth architecture. Remineralization processes are a natural protective feature of saliva against the formation of tooth cavities, as saliva is supersaturated with respect to calcium phosphate tooth mineral salts. Remineralization is accelerated by fluoride ions in solution which increase local supersaturation with respect to fluoridated calcium phosphate deposition. Fluoride uptake or fluoridation refers to the acquisition of fluoride into tooth substrates resulting from topical treatments with fluoride agents. Often, but not always, remineralized teeth from treatments exhibit increases in fluoride uptake and retention. Demineralization is the process of mineral loss from teeth caused by plaque acids or dietary acids. Demineralization can occur on tooth surfaces or below tooth surfaces depending upon the composition of the acids, concentration and pH. Moreover the teeth with increased remineralization and fluoride uptake and retention also exhibit superior resistance to acid demineralization. The processes of fluoride incorporation into teeth, remineralization and resistance to demineralization represent primary mechanisms toward the reduction of tooth decay or other acid insults.

In addition to fluoride agents, it is also advantageous to incorporate antimicrobial agents in oral care compositions in order to control plaque bacteria and prevent plaque formation and acid production, which is a pre-requisite step of the caries process.

Thus daily oral care at home requires products with multiple ingredients working by different mechanisms to provide the complete range of therapeutic and aesthetic benefits, including anticaries, antimicrobial, antigingivitis, antiplaque, antisensitivity, anticalculus and anti-erosion, as well as anti-odor, mouth refreshment and moisturization, stain removal, stain control and tooth whitening. Formulating oral care products that contain different ingredients to provide the required range of benefits therefore presents a challenge in that these ingredients need to act in concert and not interfere with each other's activity. The present invention is thus directed to oral care compositions comprising selected organophosphate compounds that provide protection against tooth erosion and tooth wear in combination with one or more oral care actives including fluoride agents, antiplaque/antimicrobial agents and anticalculus agents.

SUMMARY OF THE INVENTION

The present invention relates to oral care compositions comprising selected surface-active organophosphate compounds to provide protection of teeth from erosion caused by the action of chemicals, such as harsh abrasives and acids. The surface-active organophosphate compounds are substantive to teeth, the phosphate groups binding the calcium in teeth and thus preventing loss of calcium from dissolution when contacted with acids. The organophosphate compound may also deposit a protective surface coating that prevents contact of teeth with erosive challenges. Selected organophosphate compounds contain one or more phosphate groups and are combined in an oral care composition with one or more of a fluoride ion agent, an antimicrobial agent preferably selected from quaternary ammonium compounds and polyvalent metal salts, an anticalculus agent and additional surfactant, to provide benefits including superior anti-erosion, anticaries, antiplaque and anti-staining as demonstrated by enhanced fluoride uptake, remineralization, resistance to acid demineralization and antimicrobial activities, resulting in improved overall tooth health, structural integrity and appearance.

These and other features, aspects, and advantages of the present invention will become evident to those skilled in the art from the detailed description which follows.

DETAILED DESCRIPTION OF THE INVENTION

While the specification concludes with claims particularly pointing out and distinctly claiming the invention, it is believed that the present invention will be better understood from the following description.

All percentages and ratios used hereinafter are by weight of total composition, unless otherwise indicated. All percentages, ratios, and levels of ingredients referred to herein are based on the actual amount of the ingredient, and do not include solvents, fillers, or other materials with which the ingredient may be combined as a commercially available product, unless otherwise indicated.

All measurements referred to herein are made at 25° C. unless otherwise specified.

Herein, "comprising" means that other steps and other components which do not affect the end result can be added. This term encompasses the terms "consisting of" and "consisting essentially of."

As used herein, the word "include," and its variants, are intended to be non-limiting, such that recitation of items in a list is not to the exclusion of other like items that may also be useful in the materials, compositions, devices, and methods of this invention.

As used herein, the words "preferred", "preferably" and variants refer to embodiments of the invention that afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention.

By "oral care composition" is meant a product, which in the ordinary course of usage, is not intentionally swallowed for purposes of systemic administration of particular therapeutic agents, but is rather retained in the oral cavity for a time sufficient to contact substantially all of the dental surfaces and/or oral tissues for purposes of oral activity. The oral care composition may be in various forms including toothpaste, dentifrice, tooth gel, subgingival gel, mouthrinse, mousse, foam, denture product, mouthspray, lozenge, chewable tablet or chewing gum. The oral care composition may also be incorporated onto strips or films for direct application or attachment to oral surfaces.

The term "dentifrice", as used herein, includes paste, gel, liquid, powder or tablet formulations unless otherwise specified. The dentifrice composition may be a single phase composition or may be a combination of two or more separate dentifrice compositions. The dentifrice composition may be in any desired form, such as deep striped, surface striped, multilayered, having a gel surrounding a paste, or any combination thereof. Each dentifrice composition in a dentifrice comprising two or more separate dentifrice compositions may be contained in a physically separated compartment of a dispenser and dispensed side-by-side.

The term "dispenser", as used herein, means any pump, tube, or container suitable for dispensing compositions such as dentifrices.

The term "teeth", as used herein, refers to natural teeth as well as artificial teeth or dental prosthesis.

The term "orally-acceptable carrier" refer to safe and effective materials and conventional additives used in oral care compositions including but not limited to one or more of fluoride ion sources, anti-calculus or anti-tartar agents, antimicrobial agents, buffers, abrasives such as silica, alkali metal bicarbonate salts, thickening materials, humectants, water, surfactants, titanium dioxide, flavor system, sweetening agents, xylitol, and coloring agents.

Active and other ingredients useful herein may be categorized or described by their cosmetic and/or therapeutic benefit or their postulated mode of action or function. However, it is to be understood that the active and other ingredients useful herein can, in some instances, provide more than one cosmetic and/or therapeutic benefit or function or operate via more than one mode of action. Therefore, classifications herein are made for the sake of convenience and are not intended to limit an ingredient to the particularly stated application or applications listed.

Herein, the terms "tartar" and "calculus" are used interchangeably and refer to mineralized dental plaque biofilms.

The present invention relates to use of oral compositions containing selected surface active organophosphate compounds in combination with one or more of fluoride ion agents; antimicrobial agents preferably selected from cationic types such as cetylpyridinium chloride (CPC), domiphen bromide and polyvalent metal ions including stannous, zinc and copper; and anticalculus agents such as inorganic polyphosphates. The compositions also comprise one or more surfactants preferably anionic, cationic or amphoteric types. The present compositions provide effective protection against dental erosion derived from binding of calcium minerals in teeth (hydroxyapatite) and/or deposition on the tooth surface of a protective surface coating comprised of the organophosphate compound. The protective surface coating provides control of tooth surface characteristics including modification of surface hydrophilic and hydrophobic properties and resistance to acid attack. The present surface-active organophosphate compounds may also provide desired surface conditioning effects including: 1) effective desorption of portions of undesirable adsorbed pellicle proteins, in particular those associated with tooth stain binding, calculus development and attraction of undesirable microbial species and 2) maintaining surface conditioning effects and control of pellicle film for extended periods following product use, including post brushing and throughout more extended periods. The effect of modifying the surface hydrophilic and hydrophobic properties can be measured in terms of changes in water contact angles, a relative decrease indicating a more hydrophilic surface and a relative increase indicating a more hydrophobic surface. It has been discovered that the surface hydrophilic and hydrophobic properties need to be balanced to optimize delivery of benefits from the present compositions comprising the surface-active organophosphate compounds. Many of these preferred organophosphate compounds also provide tartar control or antistain/whitening or surface conditioning activities, hence providing multiple clinical actions in improving overall health and structure of teeth as well as appearance and tactile impression of teeth.

The surface active organophosphate agents have a strong affinity for enamel surface and have sufficient surface binding propensity to desorb pellicle proteins and remain affixed to enamel surfaces. Suitable examples of organophosphate compounds are mono-, di- or triesters represented by the following general structure wherein $Z^1$, $Z^2$, or $Z^3$ may be identical or different, at least one being an organic moiety, preferably selected from linear or branched, alkyl or alkenyl group of from 1 to 22 carbon atoms, optionally substituted by one or more phosphate groups; alkoxylated alkyl or alkenyl, (poly)saccharide, polyol or polyether group.

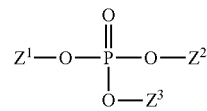

Some preferred agents include alkyl or alkenyl phosphate esters represented by the following structure:

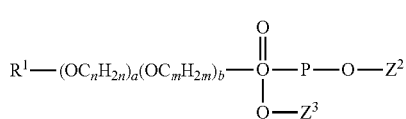

wherein $R^1$ represents a linear or branched, alkyl or alkenyl group of from 6 to 22 carbon atoms, optionally substituted by one or more phosphate groups; n and m, are individually and separately, 2 to 4, and a and b, individually and separately, are 0 to 20; $Z^2$ and $Z^3$ may be identical or different, each represents hydrogen, alkali metal, ammonium, protonated alkyl amine or protonated functional alkyl amine such as an alkanolamine, or a $R^1$—$(OC_nH_{2n})_a(OC_mH_{2m})_b$— group. Examples of suitable agents include alkyl and alkyl(poly)alkoxy phosphates such as lauryl phosphate (tradenames MAP 230K and MAP 230T from Croda); PPG5 ceteareth-10 phosphate (available from Croda under the tradename Crodaphos SG); Laureth-1 phosphate (tradenames MAP L210 from Rhodia, Phosten HLP-1 from Nikkol Chemical or Sunmaep L from Sunjin); Laureth-3 phosphate (tradenames MAP L130 from Rhodia or Foamphos L-3 from Alzo or Emphiphos DF 1326 from Huntsman Chemical); Laureth-9 phosphate (tradename Foamphos L-9 from Alzo); Trilaureth-4 phosphate (tradenames Hostaphat KL 340D from Clariant or TLP-4 from Nikkol Chemical); C12-18 PEG 9 phosphate (tradename Crafol AP261 from Cognis); Sodium dilaureth-10 phosphate (tradename DLP-10 from Nikkol Chemical). Particularly preferred agents are polymeric, for example those containing repeating alkoxy groups as the polymeric portion, in particular 3 or more ethoxy, propoxy isopropoxy or butoxy groups.

Additional suitable polymeric organophosphate agents include dextran phosphate, polyglucoside phosphate, alkyl polyglucoside phosphate, polyglyceryl phosphate, alkyl polyglyceryl phosphate, polyether phosphates and alkoxylated polyol phosphates. Some specific examples are PEG phosphate, PPG phosphate, alkyl PPG phosphate, PEG/PPG phosphate, alkyl PEG/PPG phosphate, PEG/PPG/PEG phosphate, dipropylene glycol phosphate, PEG glyceryl phosphate, PBG (polybutylene glycol) phosphate, PEG cyclodextrin phosphate, PEG sorbitan phosphate, PEG alkyl sorbitan phosphate, and PEG methyl glucoside phosphate.

Suitable non-polymeric phosphates include alkyl mono glyceride phosphate, alkyl sorbitan phosphate, alkyl methyl glucoside phosphate, alkyl sucrose phosphates.

Particularly preferred organophosphates for use as antierosion agents are those that are compatible and stable with other components of the oral care composition such as fluoride and cationic agents specifically antimicrobials such as cetylpyridinium chloride (CPC), domiphen bromide and metal ions such as stannous, copper and zinc, thus permitting simple single phase dentifrice or mouthrinse formulations.

Even more importantly, the organophosphate agent will not interfere with the activity of the other actives, specifically their fluoridation, mineralization and antimicrobial activities as demonstrated in the examples below.

The amount of organophosphate agent required is an effective amount to provide the protection from erosion due to acid or abrasive challenges. Preferably, the protection will last for at least about an hour after use of the composition. An effective amount of organophosphate agent will typically be from about 0.01% to about 35%, preferably from about 0.035% to about 20%, more preferably from about 0.035% to about 10%, and most preferably from about 0.035% to about 5%, by weight of the total oral composition.

The present compositions also comprise one or more of a fluoride ion source; an antimicrobial agent, preferably a cationic antimicrobial agent such as quaternary ammonium compounds and polyvalent metal ions; and an anticalcus agent. These and other optional components (collectively referred to as orally acceptable carriers or excipients) of the present compositions are described in the following paragraphs along with non-limiting examples. Orally acceptable carrier materials include one or more compatible solid or liquid excipients or diluents which are suitable for topical oral administration. By "compatible" is meant that the components of the composition are capable of being commingled without interaction in a manner which would substantially reduce composition stability and/or efficacy. Suitable carriers or excipients are well known in the art. Their selection will depend on secondary considerations like taste, cost, and shelf stability, etc.

Fluoride Source

It is common to have a fluoride compound present in dentifrices and other oral compositions in an amount sufficient to give a fluoride ion concentration in the composition of from about 0.0025% to about 5.0% by weight, preferably from about 0.005% to about 2.0% by weight to provide anticaries effectiveness. As discussed above, prevention of caries is essential for overall tooth health and integrity. A wide variety of fluoride ion-yielding materials can be employed as sources of soluble fluoride in the present compositions. Examples of suitable fluoride ion-yielding materials are found in U.S. Pat. No. 3,535,421 to Briner et al. and U.S. Pat. No. 3,678,154 to Widder et al. Representative fluoride ion sources include: stannous fluoride, sodium fluoride, potassium fluoride, amine fluoride, sodium monofluorophosphate, indium fluoride and many others.

Antimicrobial Agent

The present compositions may include an antimicrobial agent, preferably a quaternary ammonium antimicrobial agent to provide bactericidal efficacy, i.e., effectiveness in killing, and/or altering metabolism, and/or suppressing the growth of, microorganisms which cause topically-treatable infections and diseases of the oral cavity, such as plaque, caries, gingivitis, and periodontal disease.

The antimicrobial quaternary ammonium compounds used in the compositions of the present invention include those in which one or two of the substitutes on the quaternary nitrogen has a carbon chain length (typically alkyl group) from about 8 to about 20, typically from about 10 to about 18 carbon atoms while the remaining substitutes (typically alkyl or benzyl group) have a lower number of carbon atoms, such as from about 1 to about 7 carbon atoms, typically methyl or ethyl groups. Dodecyl trimethyl ammonium bromide, tetradecylpyridinium chloride, domiphen bromide, N-tetradecyl-4-ethyl pyridinium chloride, dodecyl dimethyl(2-phenoxyethyl) ammonium bromide, benzyl dimethoylstearyl ammonium chloride, cetylpyridinium chloride, quaternized 5-amino-1,3-bis(2-ethyl-hexyl)-5-methyl hexa hydropyrimidine, benzalkonium chloride, benzethonium chloride and methyl benzethonium chloride are exemplary of typical quaternary ammonium antibacterial agents. Other compounds are bis[4-(R-amino)-1-pyridinium]alkanes as disclosed in U.S. No. 4,206,215, Jun. 3, 1980 to Bailey. The pyridinium compounds are the preferred quaternary ammonium compounds, particularly preferred being cetylpyridinium, or tetradecylpyridinium halide salts (i.e., chloride, bromide, fluoride and iodide). Most preferred is cetylpyridinium chloride. The quaternary ammonium antimicrobial agents are included in the present invention at levels of at least about 0.035%, preferably from about 0.045% to about 1.0%, more preferably from about 0.05% to about 0.10% by weight of the composition.

As described in commonly assigned application WO 05/072693, the bioavailability and activity of quaternary ammonium antimicrobials are negatively affected particularly by anionic surfactants, which are common ingredients of oral care formulations. Thus, it is particularly surprising that certain of the present surface-active and anionic organophosphate compounds would be compatible with quaternary ammonium antimicrobials such as CPC, in that the bioavailability and antimicrobial activity are not significantly affected.

The present compositions may comprise a metal ion source that provides stannous ions, zinc ions, copper ions, or mixtures thereof as antimicrobial agent. The metal ion source can be a soluble or a sparingly soluble compound of stannous, zinc, or copper with inorganic or organic counter ions. Examples include the fluoride, chloride, chlorofluoride, acetate, hexafluorozirconate, sulfate, tartrate, gluconate, citrate, malate, glycinate, pyrophosphate, metaphosphate, oxalate, phosphate, carbonate salts and oxides of stannous, zinc, and copper.

Stannous, zinc and copper ions have been found to help in the reduction of gingivitis, plaque, sensitivity, and improved breath benefits. An effective amount is defined as from at least about 50 ppm to about 20,000 ppm metal ion of the total composition, preferably from about 500 ppm to about 15,000 ppm. More preferably, metal ions are present in an amount from about 3,000 ppm to about 13,000 ppm and even more preferably from about 5,000 ppm to about 10,000 ppm. This is the total amount of metal ions (stannous, zinc, copper and mixtures thereof) for delivery to the tooth surface.

Dentifrices containing stannous salts, particularly stannous fluoride and stannous chloride, are described in U.S. Pat. No. 5,004,597 to Majeti et al. Other descriptions of stannous salts are found in U.S. Pat. No. 5,578,293 issued to Prencipe et al. and in U.S. Pat. No. 5,281,410 issued to Lukacovic et al. In addition to the stannous ion source, other ingredients needed to stabilize the stannous may also be included, such as the ingredients described in Majeti et al. and Prencipe et al.

The preferred stannous salts are stannous fluoride and stannous chloride dihydrate. Other suitable stannous salts include stannous acetate, stannous tartrate and sodium stannous citrate. Examples of suitable zinc ion sources are zinc oxide, zinc sulfate, zinc chloride, zinc citrate, zinc lactate, zinc gluconate, zinc malate, zinc tartrate, zinc carbonate, zinc phosphate, and other salts listed in U.S. Pat. No. 4,022,880. Zinc citrate and zinc lactate are particularly preferred. Examples of suitable copper ion sources are listed in U.S. Pat. No. 5,534,243. The combined metal ion source(s) will be present in an amount of from about 0.05% to about 11%, by weight of the final composition. Preferably, the metal ion sources are present in an amount of from about 0.5 to about 7%, more preferably from about 1% to about 5%. Preferably, the stannous salts may be present in an amount of from about 0.1 to about 7%, more preferably from about 1% to about 5%, and most preferably from about 1.5% to about 3% by weight of the total composition. The amount of zinc or copper salts used in the present invention ranges from about 0.01 to about 5%, preferably from about 0.05 to about 4%, more preferably from about 0.1 to about 3.0%.

The present invention may also include other antimicrobial agents including non-cationic antimicrobial agents such as halogenated diphenyl ethers, phenolic compounds including phenol and its homologs, mono and poly-alkyl and aromatic halophenols, resorcinol and its derivatives, xylitol, bisphenolic compounds and halogenated salicylanilides, benzoic esters, and halogenated carbanilides. Also useful as antimicrobials are enzymes, including endoglycosidase, papain, dextranase, mutanase, and mixtures thereof. Such agents are disclosed in U.S. Pat. No. 2,946,725, Jul. 26, 1960, to Norris et al. and in U.S. Pat. No. 4,051,234, Sep. 27, 1977 to Gieske et al. Examples of antimicrobial agents include chlorhexidine, triclosan, triclosan monophosphate, and flavor oils such as thymol. Triclosan and other agents of this type are disclosed in Parran, Jr. et al., U.S. Pat. No. 5,015,466, issued May 14, 1991, and U.S. Pat. No. 4,894,220, Jan. 16, 1990 to Nabi et al. These agents may be present at levels of from about 0.01% to about 1.5%, by weight of the dentifrice composition.

Anticalculus Agent

The present compositions may optionally include an anticalculus agent, such as a pyrophosphate salt as a source of pyrophosphate ion. The pyrophosphate salts useful in the present compositions include the mono-, di- and tetraalkali metal pyrophosphate salts and mixtures thereof. Disodium dihydrogen pyrophosphate ($Na_2H_2P_2O_7$), sodium acid pyrophosphate, tetrasodium pyrophosphate ($Na_4P_2O_7$), and tetrapotassium pyrophosphate ($K_4P_2O_7$) in their unhydrated as well as hydrated forms are the preferred species. In compositions of the present invention, the pyrophosphate salt may be present in one of three ways: predominately dissolved, predominately undissolved, or a mixture of dissolved and undissolved pyrophosphate.

Compositions comprising predominately dissolved pyrophosphate refer to compositions where at least one pyrophosphate ion source is in an amount sufficient to provide at least about 0.025% free pyrophosphate ions. The amount of free pyrophosphate ions may be from about 1% to about 15%, from about 1.5% to about 10% in one embodiment, and from about 2% to about 6% in another embodiment. Free pyrophosphate ions may be present in a variety of protonated states depending on the pH of the composition.

Compositions comprising predominately undissolved pyrophosphate refer to compositions containing no more than about 20% of the total pyrophosphate salt dissolved in the composition, preferably less than about 10% of the total pyrophosphate dissolved in the composition. Tetrasodium pyrophosphate salt is a preferred pyrophosphate salt in these compositions. Tetrasodium pyrophosphate may be the anhydrous salt form or the decahydrate form, or any other species stable in solid form in the dentifrice compositions. The salt is in its solid particle form, which may be its crystalline and/or amorphous state, with the particle size of the salt preferably being small enough to be aesthetically acceptable and readily soluble during use. The amount of pyrophosphate salt useful in making these compositions is any tartar control effective amount, generally from about 1.5% to about 15%, preferably from about 2% to about 10%, and most preferably from about 3% to about 8%, by weight of the dentifrice composition.

Compositions may also comprise a mixture of dissolved and undissolved pyrophosphate salts. Any of the above mentioned pyrophosphate salts may be used.

The pyrophosphate salts are described in more detail in *Kirk-Othmer Encyclopedia of Chemical Technology*, Third Edition, Volume 17, Wiley-Interscience Publishers (1982).

Optional agents to be used in place of or in combination with the pyrophosphate salt include such known materials as longer chain (3 or more) polyphosphates including tripolyphosphate, tetrapolyphosphate and hexametaphosphate; synthetic anionic polymers, including polyacrylates and copolymers of maleic anhydride or acid and methyl vinyl ether (e.g., Gantrez), as described, for example, in U.S. Pat. No. 4,627,977, to Gaffar et al. as well as, e.g., polyamino propane sulfonic acid (AMPS), diphosphonates (e.g., EHDP; AHP), polypeptides (such as polyaspartic and polyglutamic acids), and mixtures thereof.

Other Active Agents

Still another active agent that may be included in the present compositions is a tooth bleaching active selected from the group consisting of peroxides, perborates, percarbonates, peroxyacids, persulfates, and combinations thereof. Suitable peroxide compounds include hydrogen peroxide, urea peroxide, calcium peroxide, sodium peroxide, zinc peroxide and mixtures thereof. A preferred percarbonate is sodium percarbonate. Preferred persulfates are oxones.

Preferred peroxide sources for use in dentifrice formulations are calcium peroxide and urea peroxide. Hydrogen peroxide and urea peroxide are preferred for use in mouthrinse formulations. The following amounts represent the amount of peroxide raw material, although the peroxide source may contain ingredients other than the peroxide raw material. The present composition may contain from about 0.01% to about 30%, preferably from about 0.1% to about 10%, and more preferably from about 0.5% to about 5% of a peroxide source, by weight of the composition.

In addition to whitening, the peroxide also provides other benefits to the oral cavity. It has long been recognized that hydrogen peroxide and other peroxygen-compounds are effective in curative and/or prophylactic treatments with respect to caries, dental plaque, gingivitis, periodontitis, mouth odor, recurrent aphthous ulcers, denture irritations, orthodontic appliance lesions, postextraction and postperiodontal surgery, traumatic oral lesions and mucosal infections, herpetic stomatitis and the like. Peroxide-containing agents in the oral cavity exert a chemomechanical action generating thousands of tiny oxygen bubbles produced by interaction with tissue and salivary enzymes. The swishing action of a mouthrinse enhances this inherent chemomechanical action. Such action has been recommended for delivery of other agents into infected gingival crevices. Peroxide mouthrinses thus prevent colonization and multiplication of anaerobic bacteria known to be associated with periodontal disease.

Another optional active agent that may be added to the present compositions is a dentinal desensitizing agent to control hypersensitivity, such as salts of potassium, calcium, strontium and tin including nitrate, chloride, fluoride, phosphates, pyrophosphate, polyphosphate, citrate, oxalate and sulfate.

Tooth Substantive Agent

The present invention may include a tooth substantive agent such as polymeric surface active agents (PMSA's), which are polyelectrolytes, more specifically anionic polymers. The PMSA's contain anionic groups, e.g., phosphate, phosphonate, carboxy, or mixtures thereof, and thus, have the capability to interact with cationic or positively charged entities. The "mineral" descriptor is intended to convey that the surface activity or substantivity of the polymer is toward mineral surfaces such as calcium phosphate minerals in teeth.

PMSA's are useful in the present compositions because of their stain prevention benefit. It is believed the PMSA's provide a stain prevention benefit because of their reactivity or substantivity to mineral surfaces, resulting in desorption of portions of undesirable adsorbed pellicle proteins, in particular those associated with binding color bodies that stain teeth, calculus development and attraction of undesirable microbial species. The retention of these PMSA's on teeth can also prevent stains from accruing due to disruption of binding sites of color bodies on tooth surfaces.

The ability of PMSA's to bind stain promoting ingredients of oral care products, for example, stannous ions and cationic antimicrobials, is also believed to be helpful. The PMSA will also provide tooth surface conditioning effects which produce desirable effects on surface thermodynamic properties and surface film properties, which impart improved clean feel aesthetics both during and most importantly, following rinsing or brushing. Many of these polymeric agents are also known or expected to provide tartar control benefits when applied in oral compositions, hence providing improvement in both the appearance of teeth and their tactile impression to consumers.

Suitable examples of such polymers are polyelectrolytes such as condensed phosphorylated polymers; polyphosphonates; copolymers of phosphate- or phosphonate-containing monomers or polymers with other monomers such as ethylenically unsaturated monomers and amino acids or with other polymers such as proteins, polypeptides, polysaccharides, poly(acrylate), poly(acrylamide), poly(methacrylate), poly(ethacrylate), poly(hydroxyalkylmethacrylate), poly(vinyl alcohol), poly(maleic anhydride), poly(maleate) poly(amide), poly(ethylene amine), poly(ethylene glycol), poly(propylene glycol), poly(vinyl acetate) and poly(vinyl benzyl chloride); polycarboxylates and carboxy-substituted polymers; and mixtures thereof. Suitable polymeric mineral surface active agents include the carboxy-substituted alcohol polymers described in U.S. Pat. Nos. 5,292,501; 5,213,789, 5,093,170; 5,009,882; and 4,939,284; all to Degenhardt et al. and the diphosphonate-derivatized polymers in U.S. Pat. No. 5,011,913 to Benedict et al; the synthetic anionic polymers including polyacrylates and copolymers of maleic anhydride or acid and methyl vinyl ether (e.g., Gantrez), as described, for example, in U.S. Pat. No. 4,627,977, to Gaffar et al. A preferred polymer is diphosphonate modified polyacrylic acid. Polymers with activity must have sufficient surface binding propensity to desorb pellicle proteins and remain affixed to enamel surfaces. For tooth surfaces, polymers with end or side chain phosphate or phosphonate functions are preferred although other polymers with mineral binding activity may prove effective depending upon adsorption affinity.

Additional examples of suitable phosphonate containing polymeric mineral surface active agents include the geminal diphosphonate polymers disclosed as anticalculus agents in U.S. Pat. No. 4,877,603 to Degenhardt et al; phosphonate group containing copolymers disclosed in U.S. Pat. No. 4,749,758 to Dursch et al. and in GB 1,290,724 (both assigned to Hoechst) suitable for use in detergent and cleaning compositions; and the copolymers and cotelomers disclosed as useful for applications including scale and corrosion inhibition, coatings, cements and ion-exchange resins in U.S. Pat. No. 5,980,776 to Zakikhani et al. and U.S. Pat. No. 6,071,434 to Davis et al. Additional polymers include the water-soluble copolymers of vinylphosphonic acid and acrylic acid and salts thereof disclosed in GB 1,290,724 wherein the copolymers contain from about 10% to about 90% by weight vinylphosphonic acid and from about 90% to about 10% by weight acrylic acid, more particularly wherein the copolymers have a weight ratio of vinylphosphonic acid to acrylic acid of 70% vinylphosphonic acid to 30% acrylic acid; 50% vinylphosphonic acid to 50% acrylic acid; or 30% vinylphosphonic acid to 70% acrylic acid. Other suitable polymers include the water soluble polymers disclosed by Zakikhani and Davis prepared by copolymerizing diphosphonate or polyphosphonate monomers having one or more unsaturated C=C bonds (e.g., vinylidene-1,1-diphosphonic acid and 2-(hydroxyphosphinyl)ethylidene-1,1-diphosphonic acid), with at least one further compound having unsaturated C=C bonds (e.g., acrylate and methacrylate monomers). Suitable polymers include the diphosphonate/acrylate polymers supplied by Rhodia under the designation ITC 1087 (Average MW 3000-60,000) and Polymer 1154 (Average MW 6000-55,000).

A preferred PMSA is a polyphosphate. A polyphosphate is generally understood to consist of two or more phosphate molecules arranged primarily in a linear configuration, although some cyclic derivatives may be present. Although pyrophosphates (n=2) are technically polyphosphates, the polyphosphates desired are those having around three or more phosphate groups so that surface adsorption at effective concentrations produces sufficient non-bound phosphate functions, which enhance the anionic surface charge as well as hydrophilic character of the surfaces. The inorganic polyphosphate salts desired include tripolyphosphate, tetrapolyphosphate and hexametaphosphate, among others. Polyphosphates larger than tetrapolyphosphate usually occur as amorphous glassy materials. Preferred in this invention are the linear polyphosphates having the formula:

$$XO(XPO_3)_nX$$

wherein X is sodium, potassium or ammonium and n averages from about 3 to about 125. Preferred polyphosphates are those having n averaging from about 6 to about 21, such as those commercially known as Sodaphos (n≈6), Hexaphos (n≈13), and Glass H (n≈21) and manufactured by FMC Corporation and Astaris. These polyphosphates may be used alone or in combination. Polyphosphates are susceptible to hydrolysis in high water formulations at acid pH, particularly below pH 5. Thus it is preferred to use longer-chain polyphosphates, in particular Glass H with an average chain length of about 21. It is believed such longer-chain polyphosphates when undergoing hydrolysis produce shorter-chain polyphosphates which are still effective to deposit onto teeth and provide a stain preventive benefit.

Other polyphosphorylated compounds may be used in addition to or instead of the polyphosphate, in particular polyphosphorylated inositol compounds such as phytic acid, myo-inositol pentakis(dihydrogen phosphate); myo-inositol tetrakis(dihydrogen phosphate), myo-inositol trikis(dihydrogen phosphate), and an alkali metal, alkaline earth metal or ammonium salt thereof. Preferred herein is phytic acid, also known as myo-inositol 1,2,3,4,5,6-hexakis (dihydrogen phosphate) or inositol hexaphosphoric acid, and its alkali metal, alkaline earth metal or ammonium salts. Herein, the term "phytate" includes phytic acid and its salts as well as the other polyphosphorylated inositol compounds.

The amount of tooth substantive agent will typically be from about 0.1% to about 35% by weight of the total oral composition. In dentifrice formulations, the amount is preferably from about 2% to about 30%, more preferably from about 5% to about 25%, and most preferably from about 6% to about 20%. In mouthrinse compositions, the amount of tooth substantive agent is preferably from about 0.1% to 5% and more preferably from about 0.5% to about 3%.

In addition to creating the surface modifying effects, the tooth substantive agent may also function to solubilize insoluble salts. For example, Glass H has been found to solubilize insoluble stannous salts. Thus, in compositions containing stannous fluoride for example, Glass H contributes to decreasing the stain promoting effect of stannous.

Chelating Agents

Another optional agent is a chelating agent, also called sequestrants, such as gluconic acid, tartaric acid, citric acid and pharmaceutically-acceptable salts thereof. Chelating agents are able to complex calcium found in the cell walls of the bacteria. Chelating agents can also disrupt plaque by removing calcium from the calcium bridges which help hold this biomass intact. However, it is not desired to use a chelating agent which has an affinity for calcium that is too high, as this may result in tooth demineralization, which is contrary to the objects and intentions of the present invention. Suitable chelating agents will generally have a calcium binding constant of about $10^1$ to $10^5$ to provide improved cleaning with reduced plaque and calculus formation. Chelating agents also have the ability to complex with metallic ions and thus aid in preventing their adverse effects on the stability or appearance of products. Chelation of ions, such as iron or copper, helps retard oxidative deterioration of finished products.

Examples of suitable chelating agents are sodium or potassium gluconate and citrate; citric acid/alkali metal citrate combination; disodium tartrate; dipotassium tartrate; sodium potassium tartrate; sodium hydrogen tartrate; potassium hydrogen tartrate; sodium, potassium or ammonium polyphosphates and mixtures thereof. The chelating agent may be used from about 0.1% to about 2.5%, preferably from about 0.5% to about 2.5% and more preferably from about 1.0% to about 2.5%.

Still other chelating agents suitable for use in the present invention are the anionic polymeric polycarboxylates. Such materials are well known in the art, being employed in the form of their free acids or partially or preferably fully neutralized water soluble alkali metal (e.g. potassium and preferably sodium) or ammonium salts. Examples are 1:4 to 4:1 copolymers of maleic anhydride or acid with another polymerizable ethylenically unsaturated monomer, preferably methyl vinyl ether (methoxyethylene) having a molecular weight (M.W.) of about 30,000 to about 1,000,000. These copolymers are available for example as Gantrez AN 139 (M.W. 500,000), AN 119 (M.W. 250,000) and S-97 Pharmaceutical Grade (M.W. 70,000), of GAF Chemicals Corporation.

Other operative polymeric polycarboxylates include the 1:1 copolymers of maleic anhydride with ethyl acrylate, hydroxyethyl methacrylate, N-vinyl-2-pyrrolidone, or ethylene, the latter being available for example as Monsanto EMA No. 1103, M.W. 10,000 and EMA Grade 61, and 1:1 copolymers of acrylic acid with methyl or hydroxyethyl methacrylate, methyl or ethyl acrylate, isobutyl vinyl ether or N-vinyl-2-pyrrolidone. Additional operative polymeric polycarboxylates are disclosed in U.S. Pat. No. 4,138,477 to Gaffar and U.S. Pat. No. 4,183,914 to Gaffar et al. and include copolymers of maleic anhydride with styrene, isobutylene or ethyl vinyl ether; polyacrylic, polyitaconic and polymaleic acids; and sulfoacrylic oligomers of MW as low as 1,000 available as Uniroyal ND-2.

Surfactants

The present compositions will typically also comprise surfactants, also commonly referred to as sudsing agents. Suitable surfactants are those which are reasonably stable and foam throughout a wide pH range. The surfactant may be anionic, nonionic, amphoteric, zwitterionic, cationic, or mixtures thereof. Preferred surfactants or surfactant mixtures are those that are compatible with the organophosphate agent and other actives in the composition in that the activities of these components are not compromised. Anionic surfactants, such as sodium alkyl sulfate and amphoteric surfactants, such as cocoamidopropyl betaine are preferred herein.

Anionic surfactants useful herein include the water-soluble salts of alkyl sulfates having from 8 to 20 carbon atoms in the alkyl radical (e.g., sodium alkyl sulfate) and the water-soluble salts of sulfonated monoglycerides of fatty acids having from 8 to 20 carbon atoms. Sodium lauryl sulfate (SLS) and sodium coconut monoglyceride sulfonates are examples of anionic surfactants of this type. Other suitable anionic surfactants are sarcosinates, such as sodium lauroyl sarcosinate, taurates, sodium lauryl sulfoacetate, sodium lauroyl isethionate, sodium laureth carboxylate, and sodium dodecyl benzenesulfonate. Mixtures of anionic surfactants can also be employed. Many suitable anionic surfactants are disclosed by Agricola et al., U.S. Pat. No. 3,959,458. The present composition typically comprises an anionic surfactant at a level of from about 0.025% to about 9%, from about 0.05% to about 5% or from about 0.1% to about 1%.

Another suitable surfactant is one selected from the group consisting of sarcosinate surfactants, isethionate surfactants and taurate surfactants. Preferred for use herein are alkali metal or ammonium salts of these surfactants, such as the sodium and potassium salts of the following: lauroyl sarcosinate, myristoyl sarcosinate, palmitoyl sarcosinate, stearoyl sarcosinate and oleoyl sarcosinate.

Zwitterionic or amphoteric surfactants useful in the present invention include derivatives of aliphatic quaternary ammonium, phosphonium, and sulfonium compounds, in which the aliphatic radicals can be straight chain or branched, and wherein one of the aliphatic substituents contains from about 8 to 18 carbon atoms and one contains an anionic water-solubilizing group, e.g., carboxy, sulfonate, sulfate, phosphate or phosphonate. Suitable betaine surfactants are disclosed in U.S. Pat. No. 5,180,577 to Polefka et al. Typical alkyl dimethyl betaines include decyl betaine or 2-(N-decyl-N,N-dimethylammonio)acetate, coco betaine or 2-(N-coco-N, N-dimethyl ammonio)acetate, myristyl betaine, palmityl betaine, lauryl betaine, cetyl betaine, cetyl betaine, stearyl betaine, etc. The amidobetaines are exemplified by cocoamidoethyl betaine, cocamidopropyl betaine (CADB), and lauramidopropyl betaine.

Cationic surfactants useful in the present invention include derivatives of quaternary ammonium compounds having one long alkyl chain containing from about 8 to 18 carbon atoms such as lauryl trimethylammonium chloride; cetyl pyridinium chloride; cetyl trimethylammonium bromide; coconut alkyltrimethylammonium nitrite; cetyl pyridinium fluoride; etc. Preferred compounds are the quaternary ammonium fluorides having detergent properties described in U.S. Pat. No. 3,535,421 to Briner et al. Certain cationic surfactants can also act as germicides in the compositions disclosed herein.

Nonionic surfactants that can be used in the compositions of the present invention include compounds produced by the condensation of alkylene oxide groups (hydrophilic in nature) with an organic hydrophobic compound which may be aliphatic or alkylaromatic in nature. Examples of suitable nonionic surfactants include the Pluronics, polyethylene oxide condensates of alkyl phenols, products derived from the condensation of ethylene oxide with the reaction product of propylene oxide and ethylene diamine, ethylene oxide condensates of aliphatic alcohols, long chain tertiary amine oxides, long chain tertiary phosphine oxides, long chain dialkyl sulfoxides and mixtures of such materials.

Abrasives

Dental abrasives useful in the compositions of the subject invention include many different materials. The material selected must be one which is compatible within the composition of interest and does not excessively abrade dentin. Suitable abrasives include, for example, silicas including gels and precipitates, insoluble sodium polymetaphosphate, hydrated alumina, calcium carbonate, dicalcium orthophosphate dihydrate, calcium pyrophosphate, tricalcium phosphate, calcium polymetaphosphate, and resinous abrasive materials such as particulate condensation products of urea and formaldehyde.

Another class of abrasives for use in the present compositions is the particulate thermo-setting polymerized resins as described in U.S. Pat. No. 3,070,510 issued to Cooley & Grabenstetter. Suitable resins include, for example, melamines, phenolics, ureas, melamine-ureas, melamine-formaldehydes, urea-formaldehyde, melamine-urea-formaldehydes, cross-linked epoxides, and cross-linked polyesters.

Silica dental abrasives of various types are preferred because of their unique benefits of exceptional dental cleaning and polishing performance without unduly abrading tooth enamel or dentine. The silica abrasive polishing materials herein, as well as other abrasives, generally have an average particle size ranging between about 0.1 to about 30 microns, and preferably from about 5 to about 15 microns. The abrasive can be precipitated silica or silica gels such as the silica xerogels described in Pader et al., U.S. Pat. No. 3,538,230 and DiGiulio, U.S. Pat. No. 3,862,307. Examples include the silica xerogels marketed under the trade name "Syloid" by the W.R. Grace & Company, Davison Chemical Division and precipitated silica materials such as those marketed by the J. M. Huber Corporation under the trade name, Zeodent®, particularly the silicas carrying the designation Zeodent® 119, Zeodent® 118, Zeodent® 109 and Zeodent® 129. The types of silica dental abrasives useful in the toothpastes of the present invention are described in more detail in Wason, U.S. Pat. No. 4,340,583; and in commonly-assigned U.S. Pat. Nos. 5,603,920; 5,589,160; 5,658,553; 5,651,958; and 6,740,311.

Mixtures of abrasives can be used such as mixtures of the various grades of Zeodent® silica abrasives listed above. The total amount of abrasive in dentifrice compositions of the subject invention typically range from about 6% to about 70% by weight; toothpastes preferably contain from about 10% to about 50% of abrasives. Dental solution, mouth spray, mouthwash and non-abrasive gel compositions of the subject invention typically contain little or no abrasive.

Flavor System

The flavor system is typically added to oral care compositions, to provide a pleasant tasting composition and to effectively mask any unpleasant taste and sensations due to certain components of the composition such as antimicrobial actives or peroxide. Pleasant tasting compositions improve user compliance to prescribed or recommended use of oral care products. The present flavor system will comprise flavor components, in particular those that have been found to be relatively stable in the presence of usual oral care product actives, carrier materials or excipients. The combination of the selected flavoring components with sensate ingredients such as coolant(s) provides a high-impact refreshing sensation with a well-rounded flavor profile.

The flavor system may comprise flavor ingredients including but not limited to peppermint oil, corn mint oil, spearmint oil, oil of wintergreen, clove bud oil, cassia, sage, parsley oil, marjoram, lemon, lime, orange, cis-jasmone, 2,5-dimethyl-4-hydroxy-3(2H)-furanone, 5-ethyl-3-hydroxy-4-methyl-2(5H)-furanone, vanillin, ethyl vanillin, anisaldehyde, 3,4-methylenedioxybenzaldehyde, 3,4-dimethoxybenzaldehyde, 4-hydroxybenzaldehyde, 2-methoxybenzaldehyde, benzaldehyde; cinnamaldehyde, hexyl cinnamaldehyde, alpha-methyl cinnamaldehyde, ortho-methoxy cinnamaldehyde, alpha-amyl cinnamaldehydepropenyl guaethol, heliotropine, 4-cis-heptenal, diacetyl, methyl-p-tert-butyl phenyl acetate, menthol, methyl salicylate, ethyl salicylate, 1-menthyl acetate, oxanone, alpha-irisone, methyl cinnamate, ethyl cinnamate, butyl cinnamate, ethyl butyrate, ethyl acetate, methyl anthranilate, iso-amyl acetate, iso-amyl butyrate, allyl caproate, eugenol, eucalyptol, thymol, cinnamic alcohol, octanol, octanal, decanol, decanal, phenylethyl alcohol, benzyl alcohol, alpha-terpineol, linalool, limonene, citral, maltol, ethyl maltol, anethole, dihydroanethole, carvone, menthone, β-damascenone, ionone, gamma decalactone, gamma nonalactone, gamma undecalactone and mixtures thereof. Generally suitable flavoring ingredients are those containing structural features and functional groups that are less prone to redox reactions. These include derivatives of flavor chemicals that are saturated or contain stable aromatic rings or ester groups. Also suitable are flavor chemicals that may undergo some oxidation or degradation without resulting in a significant change in the flavor character or profile. The flavor ingredients may be supplied in the composition as single or purified chemicals or by addition of natural oils or extracts that have preferably undergone a refining treatment to remove components that are relatively unstable and may degrade and alter the desired flavor profile, resulting in a less acceptable product from an organoleptic standpoint. Flavoring agents are generally used in the compositions at levels of from about 0.001% to about 5%, by weight of the composition.

The flavor system will typically include a sweetening agent. Suitable sweeteners include those well known in the art, including both natural and artificial sweeteners. Some suitable water-soluble sweeteners include monosaccharides, disaccharides and polysaccharides such as xylose, ribose, glucose (dextrose), mannose, galactose, fructose (levulose), sucrose (sugar), maltose, invert sugar (a mixture of fructose and glucose derived from sucrose), partially hydrolyzed starch, corn syrup solids, dihydrochalcones, monellin, steviosides, and glycyrrhizin. Suitable water-soluble artificial sweeteners include soluble saccharin salts, i.e., sodium or calcium saccharin salts, cyclamate salts, the sodium, ammonium or calcium salt of 3,4-dihydro-6-methyl-1,2,3-oxathiazine-4-one-2,2-dioxide, the potassium salt of 3,4-dihydro-6-methyl-1,2,3-oxathiazine-4-one-2,2-dioxide (acesulfame-K), the free acid form of saccharin, and the like. Other suitable sweeteners include dipeptide based sweeteners, such as L-aspartic acid derived sweeteners, such as L-aspartyl-L-phenylalanine methyl ester (aspartame) and materials described in U.S. Pat. No. 3,492,131, L-alpha-aspartyl-N-(2,2,4,4-tetramethyl-3-thietanyl)-D-alaninamide hydrate, methyl esters of L-aspartyl-L-phenylglycerin and L-aspartyl-L-2,5,dihydrophenyl-glycine, L-aspartyl-2,5-dihydro-L-phenylalanine, L-aspartyl-L-(1-cyclohexylen)-alanine, and the like. Water-soluble sweeteners derived from naturally occurring water-soluble sweeteners, such as a chlorinated derivative of ordinary sugar (sucrose), known, for example, under the product description of sucralose as well as protein based sweeteners such as *thaumatoccous danielli* (Thaumatin I and II) can be used. A composition preferably contains from about 0.1% to about 10% of sweetener, by weight.

Suitable cooling agents or coolants include a wide variety of materials such as menthol and derivatives thereof. Among synthetic coolants, many are derivatives of or are structurally related to menthol, i.e., containing the cyclohexane moiety, and derivatized with functional groups including carboxamide, ketal, ester, ether and alcohol. Examples include the ρ-menthanecarboxamide compounds such as N-ethyl-p-menthan-3-carboxamide, known commercially as "WS-3", and others in the series such as WS-5, WS-11, WS-14 and WS-30. An example of a synthetic carboxamide coolant that is structurally unrelated to menthol is N,2,3-trimethyl-2-isopropylbutanamide, known as "WS-23". Additional suitable coolants include 3-1-menthoxypropane-1,2-diol known as TK-10, isopulegol (under the tradename Coolact P) and ρ-menthane-3,8-diol (under the tradename Coolact 38D) all available from Takasago; menthone glycerol acetal known as MGA; menthyl esthers such as menthyl acetate, menthyl acetoacetate, menthyl lactate known as Frescolat® supplied by Haarmann and Reimer, and monomenthyl succinate under the tradename Physcool from V. Mane. The terms menthol and menthyl as used herein include dextro- and levorotatory isomers of these compounds and racemic mixtures thereof. TK-10 is described in U.S. Pat. No. 4,459,425, Amano et al. WS-3 and other carboxamide cooling agents are described for example in U.S. Pat. Nos. 4,136,163; 4,150,052; 4,153,679; 4,157,384; 4,178,459 and 4,230,688. Additional N-substituted ρ-menthane carboxamides are described in WO 2005/049553A1 including N-(4-cyanomethylphenyl)-ρ-menthanecarboxamide, N-(4-sulfamoylphenyl)-ρ-menthanecarboxamide, N-(4-cyanophenyl)-ρ-menthanecarboxamide, N-(4-acetylphenyl)-ρ-menthanecarboxamide, N-(4-hydroxymethylphenyl)-ρ-menthanecarboxamide and N-(3-hydroxy-4-methoxyphenyl)-ρ-menthanecarboxamide.

In addition the flavor system may include salivating agents, hydration and moisturization agents, warming agents, and numbing agents. These agents are present in the compositions at a level of from about 0.001% to about 10%, preferably from about 0.1% to about 1%, by weight of the composition. Suitable salivating agents include Jambu® manufactured by Takasago and Optaflow® from Symrise. Examples of hydration agents include polyols such as erythritol. Suitable numbing agents include benzocaine, lidocaine, clove bud oil, and ethanol. Examples of warming agents include ethanol, capsicum and nicotinate esters, such as benzyl nicotinate. Use of agents with warming effects may of course alter the cooling effect of coolants and will need to be considered, particularly in optimizing the level of coolants.

Miscellaneous Carrier Materials

Water employed in the preparation of commercially suitable oral compositions should preferably be of low ion content and free of organic impurities. Water may comprise up to about 99% by weight of the aqueous compositions herein. These amounts of water include the free water which is added plus that which is introduced with other materials, such as with sorbitol.

The present invention may also include an alkali metal bicarbonate salt, which may serve a number of functions including abrasive, deodorant, buffering and adjusting pH. Alkali metal bicarbonate salts are soluble in water and unless stabilized, tend to release carbon dioxide in an aqueous system. Sodium bicarbonate, also known as baking soda, is a commonly used bicarbonate salt. The present composition may contain from about 0.5% to about 30% by weight of an alkali metal bicarbonate salt.

The present compositions in the form of toothpastes, dentifrices and gels typically will contain some thickening material or binder to provide a desirable consistency. Preferred thickening agents are carboxyvinyl polymers, carrageenan, hydroxyethyl cellulose, and water soluble salts of cellulose ethers such as sodium carboxymethylcellulose and sodium hydroxyethyl cellulose. Natural gums such as gum karaya, xanthan gum, gum arabic, and gum tragacanth can also be used. Colloidal magnesium aluminum silicate or finely divided silica can be used as part of the thickening agent to further improve texture. Thickening agents are typically used in an amount from about 0.1% to about 15%, by weight.

Another optional component of the compositions desired herein is a humectant. The humectant serves to keep toothpaste compositions from hardening upon exposure to air and certain humectants can also impart desirable sweetness of flavor to toothpaste compositions. Suitable humectants for use in the invention include glycerin, sorbitol, polyethylene glycol, propylene glycol, and other edible polyhydric alcohols. The humectant generally comprises from about 0% to 70%, preferably from about 15% to 55%, by weight of the composition.

The pH of the present compositions may be adjusted through the use of buffering agents. Buffering agents, as used herein, refer to agents that can be used to adjust the pH of aqueous compositions such as mouthrinses and dental solutions preferably to a range of about pH 4.0 to about pH 8.0. Buffering agents include sodium bicarbonate, monosodium phosphate, trisodium phosphate, sodium hydroxide, sodium carbonate, sodium acid pyrophosphate, citric acid, and sodium citrate and are typically included at a level of from about 0.5% to about 10% by weight.

Poloxamers may be employed in the present compositions. A poloxamer is classified as a nonionic surfactant and may also function as an emulsifying agent, binder, stabilizer, and other related functions. Poloxamers are difunctional block-polymers terminating in primary hydroxyl groups with molecular weights ranging from 1,000 to above 15,000. Poloxamers are sold under the tradename of Pluronics and Pluraflo by BASF including Poloxamer 407 and Pluraflo L4370.

Other emulsifying agents that may be used include polymeric emulsifiers such as the Pemulen® series available from B.F. Goodrich, and which are predominantly high molecular weight polyacrylic acid polymers useful as emulsifiers for hydrophobic substances.

Titanium dioxide may also be added to the present compositions as coloring or opacifying agent typically at a level of from about 0.25% to about 5% by weight.

Other optional agents that may be used in the present compositions include dimethicone copolyols selected from alkyl- and alkoxy-dimethicone copolyols, such as C12 to C20 alkyl dimethicone copolyols and mixtures thereof, as aid in providing positive tooth feel benefits. Highly preferred is cetyl dimethicone copolyol marketed under the trade name Abil EM90. The dimethicone copolyol is generally present from about 0.01% to about 25%, preferably from about 0.1% to about 5 by weight.

Method of Use

The present invention also relates to methods of use to improve overall tooth health, structure and appearance via use of the present compositions, which provide benefits including erosion protection as well as one or more of caries prevention and control of bacterial activity in the oral cavity which cause undesirable conditions including plaque, calculus, gingivitis, periodontal disease and malodor. The benefits of these compositions may increase over time when the composition is used repeatedly.

The method of use or treatment herein may comprise contacting a subject's dental enamel surfaces and mucosa in the mouth with the oral compositions according to the present invention. The method may comprise brushing with a dentifrice or rinsing with a dentifrice slurry or mouthrinse. Other methods include contacting the topical oral gel, denture product, mouthspray, or other form with the subject's teeth and oral mucosa. The subject may be any person or animal whose tooth surface is contacted with the oral composition. By animal is meant to include household pets or other domestic animals, or animals kept in captivity. For example, a method of treatment may include a person brushing a dog's teeth with one of the dentifrice compositions. Another example would include rinsing a cat's mouth with an oral composition for a sufficient amount of time to see a benefit.

EXAMPLES

The following examples further describe and demonstrate embodiments within the scope of the present invention. These examples are given solely for the purpose of illustration and are not to be construed as limitations of the present invention as many variations thereof are possible without departing from the spirit and scope.

Example I

Erosion Protection

The effectiveness of compositions of the present invention containing an organophosphate was evaluated according to the following in vitro erosion cycling protocol.

Tooth (dentin or enamel) specimens are prepared by cutting 3 mm-4 mm cores from extracted, human teeth using a diamond core drill. The teeth, collected by local surgeons, are stored until use in a 5% Thymol solution maintained at room temperature. Specimens are mounted on lucite rods with a dental acrylic (Dura Base, Reliance Mfg. Co.) covering all sides except the surface. Course polishing with 600-grit silicon carbide-water slurry is used to remove approximately 50 microns of the outer specimen surface to ensure homogeneity among specimens. Specimens are then polished with gamma alumina (Buehler No. 3, B Gamma Micropolish Alumina) to a mirror-like finish.

Approximately ⅔ of the surface of each specimen is then covered with an acid resistant nail polish (placed in a mesial-distal fashion), leaving the center portion exposed as a treatment window. Covered portions remain covered with the acid-resistant nail polish throughout the experiment, serving as the control (untreated) areas for later microradiographic analysis. Specimens are randomly assigned to one of four treatment groups (4 specimens/group).

Each group of specimens is placed in 20 ml of fresh, pooled human saliva for at least one hour to form an initial layer of pellicle on the specimen surfaces prior to first day of treatment. To begin the treatment phase, aqueous solutions of the test organophosphates and dentifrice slurry (1:3) of the control fluoride toothpaste are prepared in fresh, pooled human saliva. Each treatment cycle consists of: dentifrice slurry (2 min)→rinse in deionized distilled $H_2O$→saliva (1 hour)→erosion challenge (10 min)→rinse in dd$iH_2O$→saliva. There are 4 treatments per day for a total of five treatment days. Dentifrice treatments consist of immersing the specimens into the dentifrice slurry for two minutes while specimens rotate at 75 rpm. The erosion challenge consists of soaking each treatment group in 12 ml of 1% Citric acid (at room temperature). At any time specimens are not in treatment, they remain in 20 ml of pooled, human saliva (stirred).

The saliva is refreshed 3×/day. At night, each group of specimens remains immersed in saliva (stirred at room temperature).

After 5 days of treatment, thin cross-sections (80-120 μm thick) of each specimen are removed for assessment using standardized transverse microradiography (TMR) techniques. The exposed, treated area of each specimen is assessed with respect to complete mineral loss (erosion). Results with simple aqueous solutions of various alkyl phosphate compounds are presented in Table 1 as depth (in microns) of total mineral loss from the original specimen surface using the covered (untreated) areas as anatomical reference points. For comparison, percent reduction in surface mineral loss is calculated relative to water or fluoride containing compositions.

The data show that compared to a regular fluoride toothpaste treatment, there is significantly less tooth mineral surface loss due to acid exposure when the tooth was treated with compositions containing an alkyl phosphate or alkyl ethoxy phosphate. The magnitude of surface protection effect depends on the structure of the alkyl phosphate and the corresponding reactivity in solution and with enamel surface. The solubility of alkyl phosphates in aqueous systems plays a key role on surface effects. These findings provide strong evidence of the protective nature of oral compositions containing organophosphates in their ability to protect human enamel against erosion from acidic challenge.

TABLE 1

Surface Mineral Loss

| Treatment | Surface Loss (μm) | % reduction vs. regular F control |
|---|---|---|
| Fluoride toothpaste[1] (1100 ppm F) | 33.75 | — |
| MAP 230K[2] | 10.50 | 68.89 |
| Foamphos L-3[3] | 13.25 | 60.74 |
| CrodaphosSG[4] | 18.50 | 45.19 |
| Hostaphat KL 340D[6] | 22.50 | 33.33 |
| MAP L210[5] | 25.75 | 23.70 |
| MAP L210[5] + Cocamidopropyl betaine | 17.00 | 49.63 |
| MAP L210[5] + SLS surfactant | 11.50 | 65.93 |

[1]Crest ® Cavity Toothpaste
[2]Potassium C12/13 phosphate supplied by Croda
[3]Laureth 3 phosphate supplied by Alzo, neutralized with base such as NaOH
[4]PPGS Ceteareth-10 phosphate supplied by Croda, neutralized with base such as NaOH
[5]Laureth-1 phosphate supplied by Rhodia, neutralized with NaOH
[6]Trilaureth-4 phosphate supplied by Clariant Example II Erosion Protection and Enhanced Fluoride Uptake Adsorption of any agent that tends to modify the surface properties may also impact diffusion and adsorption of other actives delivered simultaneously Fluoride, one of the key oral care actives is well known for its anti-caries benefits. This benefit is exerted via surface adsorption and diffusion of fluoride during demineralization and remineralization processes. In this experiment, compositions were evaluated for surface protection against erosion and fluoride uptake for enhanced anti-caries benefits. The treatments used in these experiments were made by adding organophosphate test materials to a regular fluoride containing toothpaste as shown in Table 2. Erosion protection is evaluated using the in vitro erosion cycling protocol described in Example 1. Fluoride uptake is measured using a pH cycling test. The protocol used in this test is essentially equivalent to the method described in R. V. Faller, et al. "*The comparative anticaries efficacy of Crest toothpaste relative to some marketed Chinese toothpastes—results of in vitro pH cycling testing,*" Int. Dent J. 1997, 47: 313-320. In the pH cycling test, discs of enamel are removed from extracted human teeth. The naturally fluoride-rich surface is removed via grinding and polishing, presenting a human enamel surface essentially free of background fluoride. Each specimen is exposed to buffered acid solutions, effecting the development of lesions that are similar to naturally occurring caries lesions. Groups of specimens are treated in human saliva, exposed for short periods to mixtures of test product/pooled human saliva, cycles of daily acid challenge, and cycles of daily saliva exposure. Upon completion of treatments, each specimen is sampled to determine the level of fluoride incorporated into each tooth (measured as µg F/cm$^2$), as fluoride incorporation has been positively correlated with caries clinical performance of various toothpaste formulations. The results of this study demonstrate enhanced deposition of fluoride into the demineralized enamel specimens from the fluoride+organophosphate containing toothpaste—relative to a control paste containing fluoride but no organophosphate.

Results of the erosion and fluoride uptake studies are summarized in Table 3. The data demonstrate that different alkyl phosphates affect fluoride uptake differently, depending upon the structure of the molecules. Alkyl phosphates that make surfaces more hydrophobic can influence fluoride uptake more than the ones that produce less hydrophobic surfaces. Formula G contained MAP 230K, which produced a relatively more hydrophobic surface and provided good erosion protection but relatively less fluoride uptake compared to Formulas C, D, E, H, I and K. These latter formulations contain alkyl phosphates that either have ethoxy groups or large polar counter ions that make them more hydrophilic and influence their behavior towards surface attachment and subsequent properties. The more hydrophilic organophosphates provided comparable anti-erosion benefits while allowing for good fluoride uptake. The data demonstrate that several formulation options can simultaneously provide anti-caries and anti-erosion efficacy. For example, Formula J or Formula E toothpastes delivered excellent fluoride uptake and provided erosion protection significantly greater than fluoride alone (Formula A).

TABLE 2

Toothpaste Formulations

| Ingredients | A | B | C | D | E | F | G | H | I | J | K |
|---|---|---|---|---|---|---|---|---|---|---|---|
| USP Water | 11.0 | 11 | 11.0 | 11.0 | 11.0 | 11.0 | 11.0 | 11.0 | 11.0 | 11.0 | 11.0 |
| Silica, dental type | 15.0 | 15.0 | 15.0 | 15.0 | 15.0 | 15.0 | 15.0 | 15.0 | 15.0 | 15.0 | 15.0 |
| NaF USP | 0.243 | 0.243 | 0.243 | 0.243 | 0.243 | 0.243 | 0.243 | 0.243 | 0.243 | 0.243 | 0.243 |
| MAP L210[5] | — | 5.0 | — | — | — | — | — | — | — | 5.0 | — |
| Foamphos L-3[3] | — | — | 5.0 | — | — | — | — | — | — | — | — |
| Foamphos L-9[7] | — | — | — | 5.0 | — | — | — | — | — | — | — |
| DLP-10[8] | — | — | — | — | 5.0 | — | — | — | — | — | — |
| KL340D[6] | — | — | — | — | — | — | — | — | — | — | 5.0 |
| MAP 230K[2] | — | — | — | — | — | 5.0 | 5.0 | — | — | — | — |
| Crodaphos SG[4] | — | — | — | — | — | — | — | 5.0 | — | — | — |
| MAP 230T[9] | — | — | — | — | — | — | — | — | 5.0 | — | — |
| Sodium saccharin | 0.13 | 0.13 | 0.13 | 0.13 | 0.13 | 0.13 | 0.13 | 0.13 | 0.13 | 0.13 | 0.13 |
| NaOH (50% soln) | 0.5 | 0.5 | 1.0 | 0.5 | 1.0 | 1.0 | 1.0 | 1.0 | 1.0 | 0.5 | 1.0 |
| CMC sodium | 0.75 | 0.75 | 0.75 | 0.75 | 0.75 | 0.75 | 0.75 | 0.75 | 0.75 | 0.75 | 0.75 |
| Titanium dioxide | 0.25 | 0.25 | 0.25 | 0.25 | 0.25 | 0.25 | 0.25 | 0.25 | 0.25 | 0.25 | 0.25 |
| Carbomer 956 | 0.30 | 0.30 | 0.30 | 0.30 | 0.30 | 0.30 | 0.30 | 0.30 | 0.30 | 0.30 | 0.30 |
| Flavor | 0.80 | 0.80 | 0.80 | 0.80 | 0.80 | 0.80 | 0.80 | 0.80 | 0.80 | 0.80 | 0.80 |
| Na lauryl sulfate (28% soln) | 4.0 | 4.0 | — | — | — | — | — | — | — | — | — |
| Cocamidopropyl Betaine (30% soln.) | — | — | — | — | — | 3.3 | — | — | — | 3.3 | — |
| Sorbitol solution | 67.0 | 62.0 | 66.0 | 66.0 | 66.0 | 62.7 | 66.0 | 66.0 | 66.0 | 62.7 | 66.0 |
| FD&C Blue #1 | 0.05 | 0.05 | 0.05 | 0.05 | 0.05 | 0.05 | 0.05 | 0.05 | 0.05 | 0.05 | 0.05 |
| Total | 100 | 100 | 100 | 100 | 100 | 100 | 100 | 100 | 100 | 100 | 100 |

[2]Potassium C12/13 phosphate supplied by Croda
[3]Laureth-3 phosphate supplied by Alzo, neutralized with base such as NaOH
[4]PPGS Ceteareth-10 phosphate supplied by Croda, neutralized with base such as NaOH
[5]Laureth-1 phosphate supplied by Rhodia, neutralized with NaOH
[6]Trilaureth-4 phosphate supplied by Clariant
[7]Laureth-9 phosphate supplied by Alzo, neutralized with base such as NaOH
[8]Sodium diLaureth-10 phosphate supplied by Nikkol Chemical
[9]Triethanolamine C12/13 phosphate supplied by Croda

TABLE 3

Surface Protection and Fluoride Uptake

| Treatment Formula | Surface Loss (µm) | Fluoride Uptake (µg/cm$^2$) |
|---|---|---|
| Formula A | 22.00 | 16.26 |
| Formula B | 10.5 | 17.64 |
| Formula C | 17.00 | 22.71 |
| Formula D | 17.75 | 21.03 |
| Formula E | 16.25 | 23.49 |
| Formula F | 17.75 | 16.99 |
| Formula G | 12.25 | 5.57 |
| Formula H | 16.00 | 16.35 |
| Formula I | * | 15.12 |
| Formula J | 16.00 | 24.58 |
| Formula K | * | 19.76 |

*Not Measured

Example III

Compatibility of Organophosphate and Polyvalent Metal Ions

Aqueous formulations of polyvalent metal antibacterial agents were prepared and evaluated for clarity, chemical content and performance when mixed with various organophosphate additives as described above. The compositions comprise stannous fluoride as an example of polyvalent metal cation in combination with sodium gluconate or sodium tripolyphosphate as stabilizer and organophosphate additives. The compositions also contained zinc. The compositions were prepared by titrating increasing amounts of additive into aqueous solutions of 0.454% stannous fluoride/0.6% sodium gluconate and 0.454% stannous fluoride/3.0% sodium tripolyphosphate. Following addition of additives, the solutions were immediately inspected for any visual changes and then analyzed for soluble tin in the supernatants after centrifugation. The results of visual inspection and soluble tin analysis are presented in Tables 4a and 4b. Dentifrice compositions comprising stannous fluoride and organophosphate agents are shown in Table 5 and erosion protection efficacy of these compositions are presented in Table 6. The formulations with Foamphos L-9 (Laureth-9 phosphate, composition N shown below) as organophosphate additive produced clear solutions of stannous fluoride and high levels of soluble stannous, indicating excellent composition stability. This combination also provided effective anti-erosion properties, better than stannous without organophosphate (composition M shown below) or Foamphos L-9 without stannous (composition D shown above). Foamphos L-9 not only stabilizes stannous fluoride, but these agents together provide enhanced anti-erosion activity.

TABLE 4a

Organophosphate Additives in Stannous Fluoride/Sodium Gluconate solutions

| Additive | Amount (%) | Soluble Tin (ppm) | Visual Inspection |
|---|---|---|---|
| Sodium lauryl sulfate | 2.0 | 2033 | Clear |
| Foamphos L-9 | 2.0 | 3145 | Slight hazy |
| DLP-10 | 2.0 | 2886 | Clear |
| Foamphos L-3 | 1.0 | 1371 | Slight precipitate |
| MAP230K | 0.2 | 2015 | Slight precipitate |
| MAP230K/Cocamidopropyl Betaine | 2.0/2.0 | 1438 | Slight precipitate |
| MAP L210 | 0.5 | 1419 | Slight precipitate |
| MAP L210/Cocamidopropyl Betaine | 1.0/1.0 | 918 | Slight precipitate |

TABLE 4b

Organophosphate Additives in Stannous Fluoride/Sodium Tripolyphosphate Solutions

| Additive | Amount (%) | Soluble Tin (ppm) | Visual Inspection |
|---|---|---|---|
| Sodium lauryl sulfate | 2.0 | 2589 | Clear |
| Foamphos L-9 | 2.0 | 2511 | Clear |
| Foamphos L-3 | 1.0 | 3496 | Slight hazy |
| MAP 230K | 0.08 | 2814 | Slight precipitate |
| MAP 230K/Cocamidopropyl Betaine | 2.0/2.0 | 2626 | Slight precipitate |
| MAP L210 | 2.0 | 1888 | Slight precipitate |
| MAP L210/Cocamidopropyl Betaine | 1.0/1.0 | 3577 | Slight hazy |

TABLE 5

Dentifrice Formulations Containing Stannous with Organophosphate Additives

| Ingredient | Formula L | Formula M | Formula N | Formula O | Formula P | Formula Q |
|---|---|---|---|---|---|---|
| Stannous Fluoride | 0.454 | 0.454 | 0.454 | 0.454 | 0.454 | 0.454 |
| Sodium Polyphosphate | 13.00 | — | — | — | — | — |
| Zinc Lactate | 2.50 | 2.50 | 2.50 | 2.50 | 2.50 | 2.50 |
| Foamphos L-9 | — | — | 1.00 | — | — | 1.00 |
| MAP L210 | — | — | — | 1.00 | — | — |
| MAP 230K | — | — | — | — | 1.00 | — |
| Silica | 25.00 | 25.00 | 25.00 | 25.00 | 25.00 | 25.00 |
| Propylene Glycol | 7.00 | 7.00 | 7.00 | 7.00 | 7.00 | 7.00 |
| Polyethylene Glycol | 7.00 | 7.00 | 7.00 | 7.00 | 7.00 | 7.00 |
| Sodium Lauryl Sulfate[a] | 3.40 | 3.40 | — | — | — | 3.40 |
| Cocamidopropyl Betaine | — | — | — | 3.30 | 3.30 | 3.30 |
| Sodium phosphate Tribasic | 1.10 | 1.10 | 1.10 | 1.10 | 1.10 | 1.10 |
| Flavor | 1.00 | 1.00 | 1.00 | 1.00 | 1.00 | 1.00 |
| Sodium Gluconate | 0.652 | 0.652 | 0.652 | 0.652 | 0.652 | 0.652 |
| Carrageenan | 0.600 | 0.600 | 0.600 | 0.600 | 0.600 | 0.600 |
| Sodium Saccharin | 0.500 | 0.500 | 0.500 | 0.500 | 0.500 | 0.500 |
| FD&C Blue #1 Dye[b] | 0.300 | 0.300 | 0.300 | 0.300 | 0.300 | 0.300 |
| Xanthan Gum | 0.250 | 0.250 | 0.250 | 0.250 | 0.250 | 0.250 |
| Glycerin | 37.24 | 50.24 | 52.64 | 49.34 | 49.34 | 20.00 |
| Water | — | — | — | — | — | 29.34 |

[a] 27.9% solution
[b] 1% solution

TABLE 6

Erosion Protection from Dentifrice Formulations Containing Stannous and Organophosphate Additives

| Treatment Product | Surface Loss (μm) | % reduction vs. F control |
|---|---|---|
| Formula A | 22.00 | — |
| Formula L | 5.50 | 75.00 |
| Formula M | 13.00 | 40.91 |
| Formula N | 9.75 | 55.68 |
| Formula O | 14.75 | 32.95 |
| Formula P | 12.75 | 42.05 |

Example IV

Compatibility of Cationic Antibacterial and Organophosphates

Like other cationic antibacterials, cetylpyridinium chloride (CPC), is not compatible with anionic additives such as anionic surfactants. CPC combined with anionic materials result in precipitation and loss of CPC bioavailability and antibacterial performance. It has been surprisingly found that a number of the present anionic organophosphate surface active agents are compatible with CPC, in particular the polymeric types, i.e., containing a polymeric alkoxy chain. These polymeric organophosphates not only produce clear aqueous solutions of CPC, but also maintain antibacterial efficacy of CPC. In addition these polymers are surface active and help mitigate CPC induced tooth staining by blocking stain components adsorption onto tooth surfaces. The following examples demonstrate effectiveness of these materials in maintaining CPC's antibacterial performance.

Mouthrinse formulations containing CPC and polymeric were made using standard liquid mixing processing in a stainless steel tank with agitator and appropriately sized impeller. The flavor oil component is emulsified with the organophosphate component in an ancillary container. The emulsion is stirred into a large volume of water until completely dispersed, followed by humectant, CPC, preservatives, sweeteners and colorants. A final water addition is made and additional mixing ensures complete dissolution of all ingredients.

The mouthrinse formulations were evaluated using a bacterial time kill assay. A 1 ml inoculum (pooled saliva from 5 donors) is added to 9 ml of test product and incubated for 30 seconds. A water control is also tested. After 30 seconds, a 1 ml aliquot is removed and added to 9 ml of neutralizing broth. A series of 1:10 dilutions are prepared and then plated in duplicate. Three different media are used: Tryptic Soy Agar (total aerobes), Brucella Blood Agar (anaerobes), and ETSA-NV Agar (Gram-negative anaerobes). Plates are incubated and then counted. Results of log reduction vs. water control for each treatment composition is presented in Table 7 below. The data show that the polymeric organophosphates with longer ethoxy chains have better compatibility with CPC, maintaining CPC bioavailability and antibacterial performance. With the organophosphate polymers with less than 3 ethoxy groups in the chain, significant loss of CPC activity is observed.

Bioavailability of the CPC in the formulations was evaluated using an in vitro Disk Retention Assay (DRA) as described in commonly assigned application WO 05/072693 and in S. J. Hunter-Rinderle, et al., "Evaluation of Cetylpyridinium Chloride-Containing Mouthwashes Using In Vitro Disk Retention and Ex Vivo Plaque Glycolysis Methods," *J. Clin. Den.*, 1997, 8:107-113. These assays are recommended for use in the proposed OTC monograph (*Federal Register* Vol. 68, No. 103 Part 356, "Oral Health Care Drug Products For Over-The-Counter Human Use; Antigingivitis/Antiplaque Drug Products; Establishment of a Monograph: Proposed Rules"). This method is designed as a performance assay to analyze mouthrinse formulations containing from about 0.03% to about 0.1% CPC to quantitatively determine the "free" ("unbound") or "bioavailable" level of CPC needed for clinical efficacy. The DRA assay measures the amount of CPC "binding" to standardized cellulose filter disks during filtration of an undiluted mouthrinse sample. The "bioavailable" CPC binds to the hydroxyl groups on the cellulose fiber during filtration while CPC, which has been rendered "non-bioavailable" (or "bound")" through interactions with mouthrinse components, simply passes through the filter paper, i.e., the positive charge on the compound is no longer available for binding to the negatively charged cellulose disks. In this way, the DRA test provides an estimate of the amount of CPC available for binding to bacteria and mucosal surfaces during use of the mouthrinse. DRA measurements of CPC availability have been positively correlated to the results of in vitro microbiological assays and in vivo germ kill tests. Historically, cellulose fibers have been used in other applications to similarly monitor biological activity of drug actives ("Dairy Products" in Official Methods of Analysis of the Association of Chemical Analytical Chemists. $13^{th}$ ed., 1980, Chapter 16:256). "Bioavailable" CPC is the amount of CPC bound to or adsorbed to cellulose disks. This is determined by measuring the differences in CPC concentration in the mouthrinse before and after exposure to standardized cellulose disks. The method has been validated and shown to perform with acceptable accuracy, precision, and selectivity.

TABLE 7

Bioavailability and Antibacterial Efficacy (Total Aerobes) of CPC in Mouthrinse Formulations CPC and Organophosphate

| Organophosphate Additive (%) | CPC (%) | Log Reduction vs. water control | % Bioavailable CPC |
|---|---|---|---|
| Foamphos L-9 (0.05%) | CPC (0.05%) | 2.76 | 90 |
| Foamphos L-9 (0.1%) | CPC (0.05%) | 2.76 | 82 |
| Foamphos L-9 (0.1%) | CPC (0.1%) | 2.76 | 75 |
| Foamphos L-3 (0.05%) | CPC (0.05%) | 2.04 | 91 |
| Foamphos L-3 (0.1%) | CPC (0.1%) | 2.05 | 82 |
| MAP 230K (0.0335%) | CPC (0.0165%) | −0.05 | * |
| MAP 230K (0.04%) | CPC (0.01%) | −0.01 | * |

*Not Measured

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An oral care composition for protecting teeth from erosion and wear due to environmental factors or intrinsic erosion in a subject in need thereof, comprising: (a) a surface-active organophosphate compound represented by the following general structure:

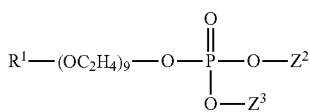

wherein $R^1$ represents a linear or branched, alkyl or alkenyl group of from 6 to 22 carbon atoms, optionally substituted by one or more phosphate groups; $Z^2$ and $Z^3$ may be identical or different, each represents hydrogen, alkali metal, ammonium, protonated C1-C4 alkyl amine or alkanolamine, or a $R^1$—$(OC_2H_4)_9$— group; and
(b) an orally acceptable carrier,
wherein an abrasive polishing agent, when optionally present in the composition, consists essentially of silica;
wherein the oral care composition further comprises a cationic antimicrobial selected from one or a mixture of cetylpyridinium chloride, and domiphen bromide; and, optionally, further comprises a member selected from the group consisting of a stannous ion source, a zinc ion source, a copper ion source, an anticalculus active selected from one or a mixture of polyphosphates having an average number of from 2 to 125 phosphate groups, or mixtures thereof.

2. A composition according to claim 1 wherein said organophosphate compound comprises laureth-9 phosphate.

3. A composition according to claim 1 wherein said composition comprises laureth-9 phosphate and cetyl pyridinium chloride.

4. A composition according to claim 1 comprising a stannous ion source.

5. A composition according to claim 1 wherein said composition comprises laureth-9-phosphate and domiphen bromide.

6. A composition according to claim 1 which is a dentifrice.

7. A dentifrice according to claim 6 wherein the antimicrobial is cetylpyridinium chloride.

8. A dentifrice according to claim 6 wherein the organophosphate compound is laureth-9-phosphate.

9. A dentifrice according to claim 6 wherein the antimicrobial is domiphen bromide.

10. A dentifrice according to claim 6 wherein the antimicrobial is a mixture of cetylpyridinium chloride and domiphen bromide.

11. A dentifrice according to claim 6 comprising a member selected from a stannous ion source, a zinc ion source, a copper ion source, and mixtures thereof.

12. An oral care composition according to claim 1 which is a mouth rinse.

13. A mouth rinse according to claim 12 wherein the antimicrobial is cetylpyridinium chloride.

14. A mouth rinse according to claim 12 wherein the organophosphate compound is laureth-9-phosphate.

15. A mouth rinse according to claim 12 wherein the antimicrobial is domiphen bromide.

16. A mouth rinse according to claim 12 wherein the antimicrobial is a mixture of cetylpyridinium chloride and domiphen bromide.

17. A mouth rinse according to claim 12 further comprising a member selected from a stannous ion source, a zinc ion source, a copper ion source, and mixtures thereof.

18. An oral care composition according to claim 1 which further comprises a fluoride ion source to provide anticaries protection.

* * * * *